United States Patent [19]

Kageyama et al.

[11] 4,055,512
[45] Oct. 25, 1977

[54] CATALYST FOR PRODUCING CYCLOOLEFIN AND METHOD FOR MAKING THE SAME

[75] Inventors: Yoichi Kageyama; Yozo Kato, both of Yokohama; Hisao Kosugi, Tokyo, all of Japan

[73] Assignee: Mitsubishi Chemical Industries Ltd., Tokyo, Japan

[21] Appl. No.: 701,496

[22] Filed: July 1, 1976

Related U.S. Application Data

[63] Continuation-in-part of Ser. No. 575,073, May 6, 1975, abandoned.

[30] Foreign Application Priority Data

May 9, 1974 Japan ............................... 49-51596
Feb. 17, 1975 Japan ............................... 50-19594

[51] Int. Cl.$^2$ .................. B01J 23/02; B01J 23/34; B01J 23/46; B01J 23/74
[52] U.S. Cl. ........................... 252/441; 252/455 R; 252/455 Z; 252/457; 252/460; 252/466 B; 252/466 PT; 252/471; 252/472; 252/473; 252/474
[58] Field of Search .................. 252/466 PT, 460, 471, 252/472, 473, 474, 455 R, 455 Z, 457, 466 B, 441; 260/667

[56] References Cited

U.S. PATENT DOCUMENTS

| | | | |
|---|---|---|---|
| 3,829,514 | 8/1974 | Zuech | 260/667 X |
| 3,829,516 | 8/1974 | Zuech et al. | 260/667 X |
| 3,912,787 | 10/1975 | Nowack et al. | 260/667 |

Primary Examiner—W. J. Shine
Attorney, Agent, or Firm—Oblon, Fisher, Spivak, McClelland & Maier

[57] ABSTRACT

A catalyst for producing a cyclomonoolefin by hydrogenating an aromatic hydrocarbon of the formula:

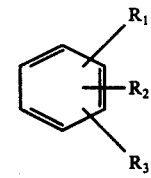

wherein $R_1$, $R_2$ and $R_3$ are the same or different and each represents hydrogen or $C_1$–$C_3$ alkyl at 100°–200° C under a hydrogen pressure of 5–100 atm. in an aqueous medium having a pH of 2–7 is prepared by (1) immersing a carrier into an aqueous solution containing at least one cation selected from the group consisting of sodium, potassium, magnesium, calcium, barium, zinc, manganese and iron to obtain a treated carrier, (2) supporting at least one metal selected from the group consisting of ruthenium and rhodium on said treated carrier, and (3) immersing the carrier impregnated with at least one metal selected from the group consisting of ruthenium and rhodium into an aqueous solution containing at least one cation selected from the group consisting of sodium, potassium, magnesium, calcium, barium, zinc manganese and iron.

11 Claims, No Drawings

4,055,512

CATALYST FOR PRODUCING CYCLOOLEFIN AND METHOD FOR MAKING THE SAME

CROSS REFERENCE TO RELATED APPLICATIONS

This application is a continuation in part of application Ser. No. 575,073, filed May 6, 1975, now abandoned.

BACKGROUND OF THE INVENTION

1. Field of the Invention

The present invention relates to a process for producing a cyclomonoolefin by hydrogenation of an aromatic hydrocarbon.

2. Description of the Prior Art

It has been known in the past to produce a cyclomonoolefin by the partial hydrogenation of the corresponding aromatic hydrocarbon in the presence of a catalyst containing Ru or Rh. Such processes include:
1. hydrogenation in the presence of a lower alcohol (U.S. Pat. No. 2,291,206);
2. hydrogenation in the presence of an organic nitrogen compound (U.S. Pat. No. 3,793,383); and
3. hydrogenation in the presence of water, an alkali and a catalyst which comprises a cation of at least one element of Group VIII of the periodic table (Japanese Patent Application Disclosure No. 42645/1972).

However, each of the processes suffers from significant disadvantages: in method (1) and (2), the selectivity and the yield of the cycloolefins are not satisfactory;

in method (3), the reaction velocity and the lifetime of the catalyst are not satisfactory. Consequently, it would be most desirable to have a method for producing a cyclomonoolefin which is free from these disadvantages.

SUMMARY OF THE INVENTION

Accordingly, it is one object of the present invention to provide a process for producing a cyclomonoolefin in high yield from an aromatic hydrocarbon.

It is another object of this invention to provide a process for producing a cyclomonoolefin which uses a catalyst enabling a high reaction velocity.

It is still another object of this invention to provide a process for producing a cyclomonoolefin which uses a catalyst having a long lifetime.

Briefly, these and other objects of the present invention which will hereinafter become apparent by the ensuing discussion have been attained by providing a catalyst for producing a cyclomonoolefin by hydrogenation of an aromatic hydrocarbon having the formula:

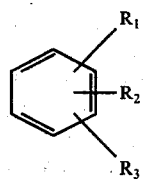

wherein $R_1$, $R_2$ and $R_3$ are the same or different and each represents hydrogen or a $C_1 - C_3$ alkyl group, at 100° - 200° C under a hydrogen pressure of 5 - 100 atm, in an aqueous medium having a pH of 2 - 7, prepared by (1) immersing a carrier into an aqueous solution containing at least one cation selected from the group consisting of sodium, potassium, magnesium, calcium, barium, zinc, manganese and iron to obtain a treated carrier, (2) supporting at least one metal selected from the group consisting of ruthenium and rhodium on said treated carrier, and (3) immersing the carrier impregnated with at least one metal selected from the group consisting of ruthenium and rhodium into an aqueous solution containing at least one cation selected from the group consisting of sodium, potassium, magnesium, calcium, barium, zinc, manganese and iron.

DETAILED DESCRIPTION OF THE PREFERRED EMBODIMENTS

The aromatic hydrocarbons used as the starting material of the invention are compounds having the formula

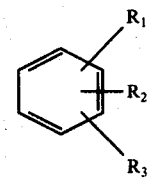

wherein $R_1$, $R_2$ and $R_3$ are the same or different and each represents hydrogen or a $C_1 - C_3$ alkyl group. Suitable aromatic hydrocarbons include benzene, toluene, o-, m- or p-xylene, ethylbenzene and the like.

The main components of the catalysts used in the invention are Ru and/or Rh. These metals can be used without being supported on a carrier, for example, in the form of ruthenium black and rhodium black. However, it is preferred that they be supported on a carrier. Suitable carriers include zeolite, silica, kieselguhr, silica-alumina, alumina, titania and the like. The supporting of Ru or Rh on the carrier can be effected by conventional methods such as dipping; condensing and drying; or precipitating. These methods may be carried out by employing an aqueous solution of a ruthenium compound and/or a rhodium compound such as the chlorides, nitrates, hydroxides, oxides and the like. The supported ruthenium compound and/or rhodium compound can be reduced by a chemical reducing agent such as formalin or sodium borohydride and the like or by hydrogen.

For the hydrogenation of the aromatic hydrocarbon of this invention, it is necessary to use an aqueous medium which is either neutral or acidic, but is not basic. The promoter used in the preparation of the catalyst of the invention is selected from the group consisting of the metals of Groups IA, and IIA of the Periodic Table, zinc, manganese, iron, ions of the foregoing metals, and ammonium ion. The metals of Group IA of the Periodic Table are preferably lithium, sodium and potassium. The metals of Group IIA of the Periodic Table are preferably magnesium, calcium, strontium and barium. The promoter is supported on the carrier by immersing the carrier into an aqueous solution of the promoter. When the promoter is used in the form of a cation in the aqueous medium, it is preferred that it be added as a chloride or sulfate. The concentration of the promoter (salt) in the aqueous solution is not critical. However, it is present in concentrations usually ranging from 0.01 - 10 mole/l preferably 0.2 - 5 mole/l, especially 0.01 wt.% relative to the saturation concentration at the temperature of the immersion treatment. This temperature should be in the range of 20° – 250° C, preferably 50° – 200° C. The duration of the treatment should be in the range of 10 minutes to 10 hours, preferably 1 to 5 hours. The atmosphere of the treatment is preferably a hydrogen atmosphere.

The catalyst of the present invention is prepared by first immersing a carrier in a solution containing a promoter and then supporting Ru and/or Rh on the treated carrier. Subsequently, the supported catalyst is subjected once again to treatment by the promoter. The resultant catalyst shows a remarkably long lifetime and high activity as substantiated by the Examples. For comparative purposes, examples of experiments are also shown in which the catalyst is prepared by immersing a carrier in a solution containing a promoter and then supporting Ru and/or Rh on the treated carrier. The treatment of the carrier with the promoter can be conducted in the same manner as the method of supporting Ru and/or Rh on the carrier except that nitrogen or air can be used as an atmosphere instead of hydrogen.

In the above treatments, the promoter is usually present on the carrier or the catalyst in amounts of 0.1 – 10 wt.%, depending upon the type of carrier. For example, when a catalyst of 1% $Ru/SiO_2$ is dipped into an aqueous solution of manganese chloride at 150° C for 150 minutes under a hydrogen pressure of 40 atm., 1.20 wt.% of manganese is supported on the catalyst. When the dipping time is 440 minutes under the same conditions, 1.24 wt.% of manganese is supported. When $SiO_2$ is dipped for 120 minutes under the same conditions, 1.11 wt.% of manganese is supported. When 1% Ru Na-Y-faujasite is dipped at 90° C for 180 minutes, 6.4 wt.% of manganese is supported.

Hydrogenation can be performed by contacting a mixture of water, the aromatic hydrocarbon and hydrogen with the modified catalyst. The hydrogenation reaction of the aromatic hydrocarbon can be carried out in a fixed bed system or a suspension bed system. The reaction temperature is usually in the range of from room temperature to 250° C, preferably 100° – 200° C. The hydrogen pressure is usually in the range of from 1 – 200 atm., preferably 5 – 100 atm. The volume ratio of the aqueous medium is usually in the range of 0.01 – 10, preferably 0.05 – 5, relative to the volume of the aromatic hydrocarbon. As previously mentioned, it is necessary to use an aqueous medium which is acidic or neutral, but not basic, preferably having a pH of 2 – 7. It is preferred to use as the aqueous medium a solution of water containing the promoter, but containing no base or acid. It is further preferred to use water containing no such agents in the case where the modified catalyst is used for the reaction.

Having generally described the invention, a more complete understanding can be obtained by reference to certain specific examples, which are included for purposes of illustration only and are not intended to be limiting unless otherwise specified.

REFERENCE EXAMPLE 1

A 1% Ru/Na-faujasite catalyst was prepared as follows. Powdered Na-Y-faujasite was dispersed in an aqueous solution of ruthenium chloride. An aqueous solution of formalin was added dropwise to the mixture with stirring and then an aqueous solution of sodium hydroxide was added dropwise, whereby ruthenium was placed on the carrier. The product was washed with water and dried at 100° C to prepare the catalyst. Into a 100 ml vertical stirring type autoclave, 1 g of the catalyst, 30 ml of benzene, 20 ml of water and 3 g of sodium chloride were charged. The reaction was conducted at 150° C under a hydrogen gas pressure of 40 atm.

REFERENCE EXAMPLE 2

The reaction was conducted in accordance with the process of Reference Example 1, except that no sodium chloride was used.

REFERENCE EXAMPLES 3 – 10

Reactions were conducted in accordance with the process of Reference Example 1, except for the addition of the salts listed in Table 1 instead of sodium chloride.

REFERENCE EXAMPLES 11 – 12

Reactions were conducted in accordance with the process of Reference Example 2, except for the use of the carriers listed in Table 1 instead of Na-Y-faujasite.

REFERENCE EXAMPLES 13 – 14

Reactions were conducted in accordance with the process of Reference Example 1, except for the use of the carriers and promoters listed in Table 1 instead of Na-Y-faujasite and sodium chloride.

REFERENCE EXAMPLE 15

Powdered silica was shaped into pellets and ruthenium chloride was supported thereon by the conventional dipping method. The mixture was calcined at 400° C for 3 hours in air and was reduced at 150° C for 2 hours under a hydrogen gas flow thereby preparing a catalyst of 1% $Ru/SiO_2$. The reaction was conducted in accordance with the process of Reference Example 1 except for use of the catalyst of this Example, manganese chloride as a promoter and a shakable type autoclave as a reactor.

In Reference Examples 1 – 15, each organic liquid phase was analyzed by gas chromatography after the reaction. As a result, the concentrations of cyclohexene, cyclohexane and unreacted benzene were determined. The results are shown in Table 1.

REFERENCE EXAMPLE 16

A modified catalyst comprising 5% $Ru/SiO_2$ was prepared as follows. A 5% $Ru/SiO_2$ catalyst was prepared in accordance with the process of Reference Example 1 except that silica was used as the carrier instead of Na-Y-faujasite and sodium borohydride was used instead of the formalin. In the autoclave, 1.7 g of the catalyst, 3.0 g of manganese chloride and 20 ml of water were charged. The mixture was maintained at 150° C for 2 hours under a hydrogen pressure of 1 atm. After cooling, the product was washed with water until no manganese chloride was left. Then, it was dried to prepare the modified catalyst. Into a 100 ml vertical stirring type autoclave, 1 g of the modified catalyst, 20 ml of water and 30 ml of benzene were charged and the reaction was conducted in accordance with the process of Reference Example 1.

TABLE 1

| | Catalyst | Promoter | Reaction time (min.) | Conversion of benzene (%) | Selectivity of cyclohexene(%) |
|---|---|---|---|---|---|
| Ref. 2 | 1% Ru/Na-Y-faujasite | none | 25 | 60 | 6.7 |
| Ref. 1 | " | NaCl | 30 | 60 | 15.0 |
| Ref. 3 | " | KCl | 30 | 60 | 16.0 |
| Ref. 4 | " | $MgCl_2 \cdot 6H_2O$ | 30 | 60 | 20.8 |
| Ref. 5 | " | $CaCl_2 \cdot 2H_2O$ | 40 | 60 | 21.3 |
| Ref. 6 | " | $ZnCl_2$ | 200 | 60 | 24.2 |
| Ref. 7 | " | $MnCl_2 \cdot 4H_2O$ | 30 | 60 | 27.5 |
| Ref. 8 | " | $MnSO_4 \cdot nH_2O$ | 30 | 60 | 17.5 |
| Ref. 9 | " | $NH_4Cl$ | 200 | 60 | 28.5 |
| Ref. 10 | " | $(NH_4)_2SO_4$ | 20 | 55 | 19.3 |
| Ref. 11 | 1% Ru/SiO$_2$-Al$_2$O$_3$ | none | 40 | 50 | 3.3 |
| Ref. 13 | " | $MgCl_2 \cdot 6H_2O$ | 200 | 75 | 10.7 |
| Ref. 12 | 1% Ru/SiO$_2$ | none | 25 | 65 | 4.6 |
| Ref. 14 | " | $MnCl_2 \cdot 4H_2O$ | 30 | 50 | 15.8 |
| Ref. 15 | "(pellets) | " | 90 | 55 | 13.3 |

REFERENCE EXAMPLE 17

A reaction was conducted in accordance with the process of Reference Example 16, except that the catalyst was not modified with an aqueous solution of manganese chloride.

REFERENCE EXAMPLES 18 – 24

Modified catalysts of 1% Ru/SiO$_2$ were prepared and reactions were conducted in accordance with the process of Reference Example 16 except that an aqueous solution of each salt shown in Table 2 was used instead of the aqueous solution of manganese chloride.

REFERENCE EXAMPLE 25

A reaction was conducted in accordance with the process of Reference Example 16 except for the use of a modified commercial catalyst of 2% Rh/Al$_2$O$_3$, which was treated with an aqueous solution of manganese chloride.

REFERENCE EXAMPLE 26

A reaction was conducted in accordance with the process of Reference Example 16 except for use of an unmodified commercial catalyst of 2% Rh/Al$_2$O$_3$.

The results of Reference Examples 16 – 26 are shown in Table 2.

fied catalyst was prepared in accordance with the process of Reference Example 16 except for the use of the modified carrier and treatment of the resulting Ru/SiO$_2$ catalyst for 3 hours under an initial hydrogen pressure of 30 atm. in a solution of manganese chloride. Into a 100 ml vertical stirring type autoclave, 1 g of the modified catalyst, 20 ml of water and 30 ml of benzene were charged. The reaction was conducted at 150° C under a hydrogen pressure of 40 atm. until a 60% conversion of benzene was effected. The time ($\theta_1$) required for the reaction was 25 minutes. The reaction mixture was cooled, and all of the organic liquid phase was removed from the autoclave and analyzed by gas chromatography. Into the autoclave, 30 ml of fresh benzene was charged and the reaction was further conducted under the same conditions until a 60% conversion of benzene was again reached. This same operation was repeated several times. In the fifth operation, the reaction time ($\theta_5$) required for providing a conversion of 60% was 28 minutes. The results of the reactions of the first and fifth operations are shown in Table 3.

The results of Examples 2 – 9 and Reference Examples 27 – 35 are also shown in Table 3.

REFERENCE EXAMPLE 27

The reaction was conducted in accordance with the process of Example 1 except that the carrier was not

TABLE 2

| | Catalyst | Promoter | Reaction time (min.) | Conversion of benzene (%) | Selectivity of cyclohexene (%) |
|---|---|---|---|---|---|
| Ref. 17 | 5% Ru/SiO$_2$ | none | 40 | 60 | 3.3 |
| Ref. 16 | " | $MnCl_2 \cdot 4H_2O$ | 54 | 60 | 38.0 |
| Ref. 18 | 1% Ru/SiO$_2$ | $ZnCl_2$ | 43 | 65 | 17.0 |
| Ref. 19 | " | $CaCl_2 \cdot 2H_2O$ | 44 | 65 | 17.0 |
| Ref. 20 | " | $FeCl_2 \cdot nH_2O$ | 49 | 45 | 20.0 |
| Ref. 21 | " | $BaCl_2 \cdot 2H_2O$ | 47 | 60 | 13.0 |
| Ref. 22 | " | $MgCl_2 \cdot 6H_2O$ | 34 | 70 | 19.0 |
| Ref. 23 | " | $MnSO_4 \cdot nH_2O$ | 39 | 65 | 22.0 |
| Ref. 24 | " | NaBr | 32 | 60 | 12.0 |
| Ref. 25 | 2% Rh/Al$_2$O$_3$ | $MnCl_2 \cdot 4H_2O$ | 55 | 65 | 10.0 |
| Ref. 26 | " | none | 16 | 60 | 1.7 |

EXAMPLE 1

A modified catalyst of 1% Ru/SiO$_2$ was prepared as follows. Into the autoclave, 13 g of silica, 75 g of manganese chloride and 50 ml of water were charged and the mixture was maintained at 150° C for 5 hours under an initial hydrogen pressure of 30 atm. After cooling, the carrier was washed with water until no manganese chloride was left. Then, it was dried at 100° C. A modified with the salt.

EXAMPLE 2

The reaction was conducted in accordance with the process of Example 1 except that the temperature used in the modification of the carrier was 50° C.

EXAMPLE 3

The reaction was conducted in accordance with the process of Example 1, except that the modification of the carrier was conducted for 1 hour in a nitrogen atmosphere at a pressure of 1 atm. instead of a hydrogen pressure of 30 atm., and that the catalyst was modified with an aqueous solution of magnesium chloride, instead of manganese chloride.

EXAMPLES 4 – 8

The reaction was conducted in accordance with the process of Example 1 except that both the carrier alone and the carrier with Ru supported thereon, i.e., the catalyst, were respectively modified with an aqueous solution of each salt of Table 3.

REFERENCE EXAMPLES 28 – 32

The reactions were respectively conducted in accordance with the processes of Examples 28 – 32 except that the carrier was not modified before the supporting operation.

REFERENCE EXAMPLE 33

Na-Y-faujasite was modified with an aqueous solution of sodium chloride in accordance with the process of Example 1 and Ru was supported thereon in accordance with the process of Reference Example 1. The reaction was repeated 5 times under the conditions of Reference Example 1 using the catalyst.

REFERENCE EXAMPLE 34

The reaction was repeated 5 times under the conditions of Reference Example 1.

EXAMPLE 9

The reaction was conducted in accordance with the process of Example 1 except that γ-alumina was used instead of silica as a carrier, and 2% of rhodium was supported instead of ruthenium.

REFERENCE EXAMPLE 35

The reaction was conducted in accordance with the process of Example 9 except that the carrier was not modified.

REFERENCE EXAMPLE 36

Into the 100 ml autoclave, 1 g of the catalyst of Reference Example 1 comprising 1% of Ru/Na-Y-faujasite, 20 ml of water, 30 ml of toluene, 3 g of manganese chloride were charged. The reaction was conducted at 150° C under a hydrogen gas pressure of 40 atm. The results are shown in Table 4.

TABLE 3

| | CATALYST | PROMOTER TREATMENT OF CARRIER | TREATMENT OF CATALYST | FIRST OPERATION $\theta_1$ (min) | SELECTIVITY OF CYCLOHEXENE (%) | FIFTH OPERATION $\theta_5$ (min) | SELECTIVITY OF CYCLOHEXENE (%) | $\theta_1/\theta_5$ |
|---|---|---|---|---|---|---|---|---|
| Exp. 1 | 1% Ru/SiO$_2$ | MnCl$_2$·4H$_2$O | MnCl$_2$·4H$_2$O | 25 | 15.9 | 28 | 17.3 | 0.89 |
| Ref. 27 | " | — | " | 44 | 30.0 | 100 | 28.7 | 0.44 |
| Exp. 2 | " | MnCl$_2$·4H$_2$O | " | 25 | 15.8 | 30 | 15.0 | 0.85 |
| Exp. 3 | " | " | MgCl$_2$·6H$_2$O | 23 | 14.4 | 28 | 14.8 | 0.82 |
| Exp. 4 | " | MgCl$_2$·6H$_2$O | " | 21 | 16.7 | 25 | 17.7 | 0.84 |
| Exp. 5 | " | ZnCl$_2$ | ZnCl$_2$ | 28 | 16.1 | 32 | 15.4 | 0.88 |
| Exp. 6 | " | FeCl$_2$·nH$_2$O | FeCl$_2$·nH$_2$O | 30 | 15.8 | 38 | 16.1 | 0.79 |
| Exp. 7 | " | BaCl$_2$·2H$_2$O | BaCl$_2$·2H$_2$O | 26 | 11.5 | 35 | 12.0 | 0.74 |
| Exp. 8 | " | MnSO$_4$·nH$_2$O | MnSO$_4$·nH$_2$O | 20 | 18.2 | 24 | 18.0 | 0.83 |
| Ref. 28 | " | — | MgCl$_2$·6H$_2$O | 40 | 25.3 | 59 | 27.6 | 0.67 |
| Ref. 29 | " | — | ZnCl$_2$ | 39 | 17.2 | 83 | 18.0 | 0.47 |
| Ref. 30 | " | — | FeCl$_2$·nH$_2$O | 47 | 18.6 | 84 | 17.8 | 0.56 |
| Ref. 31 | " | — | BaCl$_2$·2H$_2$O | 43 | 13.0 | 100 | 12.4 | 0.43 |
| Ref. 32 | " | — | MnSO$_4$·nH$_2$O | 40 | 24.4 | 84 | 23.7 | 0.48 |
| Ref. 33 | 1% Ru/NaeYe Faujasite | NaCl | — | 30 | 14.8 | 35 | 26.0 | 0.86 |
| Ref. 34 1) | " | — | — | 30 | 15.0 | 870 | 18.6 | 0.04 |
| Exp. 9 | 2% Rh/Al$_2$O$_3$ | MnCl$_2$·4H$_2$O | MnCl$_2$·4H$_2$O | 32 | 9.6 | 48 | 9.8 | 0.67 |
| Ref. 35 | " | — | " | 50 | 11.1 | 160 | 11.7 | 0.31 |

NOTE: 1)
3.0 g of sodium chloride was added to the reaction system

REFERENCE EXAMPLE 37

The reaction was conducted in accordance with the process of Reference Example 36 except that no manganese chloride was used.

REFERENCE EXAMPLE 38

Into the autoclave, 1.7 g of the catalyst of Reference Example 1 comprising 1% Ru/Na-Y-faujasite, 20 ml of water, 0.1 g of manganese chloride were charged. The catalyst was modified at 120° C for 30 minutes under a hydrogen gas pressure of 30 atm. The product was washed with water and then was dried to prepare the modified catalyst. In the autoclave, 1 g of the modified catalyst, 20 ml of water and 30 ml of toluene were charged and the reaction was conducted at 200° C under a hydrogen gas pressure of 60 atm. until a 60% conversion of toluene was effected. The reaction was repeated 5 times.

REFERENCE EXAMPLE 39

Na-Y-faujasite was modified in accordance with the process of Example 1 except that 0.5 g of manganese chloride was used instead of 7.5 g of manganese chloride. Using this modified carrier, a catalyst comprising 1% Ru/Na-Y-faujasite was prepared in accordance with Reference Example 1. This catalyst was further modified and used in a hydrogenation reaction in accordance with Reference Example 38.

The results of Reference Examples 36 – 39 are shown in Table 4.

TABLE 4

|  | CONDITION OF REACTION | FIRST OPERATION | | | FIFTH OPERATION | | |
|---|---|---|---|---|---|---|---|
|  |  | CONVERSION OF TOLUENE (%) | REACTION TIME $\theta_1$(min) | SELECTIVITY OF METHYLCYCLOHEXENE(%) | REACTION TIME $\theta_5$(min) | SELECTIVITY OF METHYLCYCLOHEXENE(%) | $\theta_1/\theta_5$ |
| Ref. 37 | 150° C 40 atm. | 50 | 50 | 4.0 |  |  |  |
| Ref. 36 | " | 65 | 110 | 30.0 |  |  |  |
| Ref. 38 | 200° C 60 atm. | 60 | 70 | 26.2 | 135 | 24.3 | 0.52 |
| Ref. 39 | " | 60 | 55 | 22.8 | 65 | 22.0 | 0.85 |

REFERENCE EXAMPLE 40

A reaction was conducted in accordance with the process of Example 36, except that the o-xylene was used instead of toluene and the reaction temperature was 180° C.

REFERENCE EXAMPLE 41

A reaction was conducted in accordance with the process of Reference Example 37 except that o-xylene was used instead of toluene and the reaction temperature was 180° C.

REFERENCE EXAMPLE 42

The reaction was conducted in accordance with the process of Reference Example 38 except that o-xylene was used instead of toluene.

The results of Reference Examples 40 - 42 are shown in Table 5.

TABLE 5

| | REACTION CONDITION | CONVERSION OF o-XYLENE | SELECTIVITY (%) | REACTION TIME (min.) |
|---|---|---|---|---|
| Ref. 41 | 180° C 40 atm. | 55 | 5.3 | 100 |
| Ref. 40 | " | 60 | 35.0 | 240 |
| Ref. 42 | 200° C 60 atm. | 35 | 29.0 | 60 |

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A catalyst for producing a cyclomonoolefin by hydrogenating an aromatic hydrocarbon of the formula:

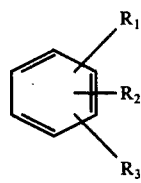

wherein $R_1$, $R_2$ and $R_3$ are the same or different and each represents hydrogen or a $C_1 - C_3$ alkyl, at 100° - 200° C under a hydrogen pressure of 5 - 100 atm in an aqueous medium having a pH of 2 - 7, prepared by a process comprising:

1. immersing a carrier into a first aqueous solution containing at least one salt whose cationic component is selected from the group consisting of sodium, potassium, magnesium, calcium, barium, zinc, manganese and iron thereby obtaining a treated carrier containing said salt and separating said salt impregnated carrier from said first aqueous solution;
2. supporting at least one ruthenium or rhodium compound on said treated carrier and reducing said compound such that ruthenium or rhodium is reduced to the metallic state; and
3. immersing the carrier supporting at least one metal selected from the group consisting of rhodium and ruthenium into a second aqueous solution containing at least one salt whose cationic component is selected from the group consisting of sodium, potassium, magnesium, calcium, barium, zinc, manganese and iron thereby obtaining a ruthenium or rhodium supported carrier which is impregnated with said salts of steps (1) and (3) and separating the resultant catalyst from said second aqueous solution.

2. The catalyst of claim 1, wherein said carrier is selected from the group consisting of zeolite, silica, silica-alumina, alumina and kieselgahr.

3. The catalyst of claim 1, wherein the concentration of said cation in said aqueous solution is 0.01 - 10 mole/liter.

4. The catalyst of claim 1, wherein said carrier is treated with manganese chloride.

5. A method for preparing a catalyst for hydrogenating an aromatic hydrocarbon having the formula

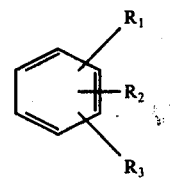

wherein $R_1$, $R_2$ and $R_3$ are the same or different and each represents hydrogen or a $C_1 - C_3$ alkyl group under hydrogen pressure of 5 - 100 atmospheres at a temperature of 100° - 200° C in an aqueous medium having a pH of 2 - 7 to a cyclomonoolefin, which comprises:

1. immersing a carrier into a first aqueous solution containing at least one salt whose cationic component is selected from the group consisting of sodium, potassium, magnesium, calcium, barium, zinc, manganese and iron thereby obtaining a treated carrier containing said salt and thereafter separating said salt impregnated carrier from said first aqueous solution;
2. supporting at least one ruthenium or rhodium compound on said treated carrier and reducing said compound such that ruthenium or rhodium is reduced to the metallic state;

3. immersing the carrier supporting at least one metal selected from the group consisting of ruthenium and rhodium into a second aqueous solution containing at least one salt whose cationic component is selected from the group consisting of sodium, potassium, magnesium, calcium, barium, zinc, manganese and iron thereby obtaining a ruthenium and/or rhodium supported carrier which is impregnated with said salts of steps (1) and (3) and separating the resultant catalyst from said second aqueous solution.

6. The method of claim 5, wherein said cation is present in said aqueous solution as a chloride salt.

7. The method of claim 5, wherein said treated carrier is prepared by immersion in an aqueous solution containing manganese chloride.

8. The method of claim 5, wherein the concentration of said cation in said aqueous medium is 0.01 – 10 mole/liter.

9. The process of claim 5, wherein said carrier is selected from the group consisting of zeolite, silica, silica-alumina, alumina and kieselgohr.

10. The method of claim 5, wherein said aromatic hydrocarbon is benzene, toluene or xylene.

11. The method of claim 5, wherein said carrier is immersed in an aqueous solution containing said cation at a temperature of 20° – 250° C.

* * * * *